(12) United States Patent
Paracchini

(10) Patent No.: US 6,500,965 B2
(45) Date of Patent: Dec. 31, 2002

(54) DRY EXTRACT WHICH IS RICH IN ISOFLAVONES IN THE FORM OF AGLYCONES AND PROCESS FOR PREPARING THE SAME

(75) Inventor: Silvano Paracchini, Muralto (CH)

(73) Assignee: Linnea SA, Riazzino (CH)

( * ) Notice: Subject to any disclaimer, the term of this patent is extended or adjusted under 35 U.S.C. 154(b) by 0 days.

(21) Appl. No.: 09/882,571

(22) Filed: Jun. 18, 2001

(65) Prior Publication Data

US 2002/0016478 A1 Feb. 7, 2002

(30) Foreign Application Priority Data

Jul. 20, 2000 (EP) .............................................. 00202599

(51) Int. Cl.⁷ ........................................... C07D 311/76
(52) U.S. Cl. ...................................... 549/403; 210/607
(58) Field of Search ......................................... 549/399

(56) References Cited

U.S. PATENT DOCUMENTS

| | | | | |
|---|---|---|---|---|
| 5,726,034 A | * | 3/1998 | Bryan et al. ................. | 435/68.1 |
| 5,763,389 A | * | 6/1998 | Shen et al. .................. | 549/403 |
| 6,015,785 A | * | 1/2000 | Shen et al. .................. | 530/370 |

FOREIGN PATENT DOCUMENTS

| WO | WO 93/23069 | 11/1993 |
|---|---|---|
| WO | WO 99/43335 | 9/1999 |
| WO | WO 99/48496 | 9/1999 |

OTHER PUBLICATIONS

R. G. Glencross, et al., "Separation and Determination of Isoflavones in the Protein Concentrate from Red Clover Leaves", Journal of the Science of Food and Agriculture, vol. 23 No. 3, 1972, pp. 371–376.

\* cited by examiner

*Primary Examiner*—Alan L. Rotman
*Assistant Examiner*—Raymond Covington
(74) *Attorney, Agent, or Firm*—Oblon, Spivak, McClelland, Maier & Neustadt, P.C.

(57) ABSTRACT

A process for extracting isoflavones from a plant material, wherein the said process comprises treating the plant material with an organic solvent, characterized in that the said extraction is preceded by a step of maceration in water. A dry extract containing, as aglycones, at least 8% (w/w) of one or more isoflavones or formula

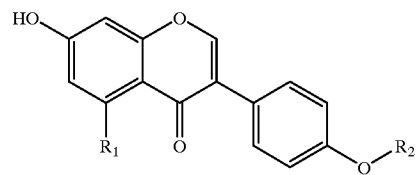

wherein
$R_1$=OH and $R_2$=H, Genistein;
$R_1$=H and $R_2$=H, Daidzein;
$R_1$=H and $R_2$=CH$_3$, Formononetin;
$R_1$=OH and $R_2$=CH$_3$, Biochanin A.

42 Claims, No Drawings

DRY EXTRACT WHICH IS RICH IN ISOFLAVONES IN THE FORM OF AGLYCONES AND PROCESS FOR PREPARING THE SAME

This application is based on European Patent Application No. 00202599.7 filed on Jul. 20, 2000, the content of which is incorporated hereinto by reference.

The present invention relates to a dry extract which is rich in isoflavones, as aglycones, and to a process for preparing the same.

More particularly, the present invention relates to a dry extract containing at least 8% (w/w) of one or more isoflavones, as aglycones, of formula

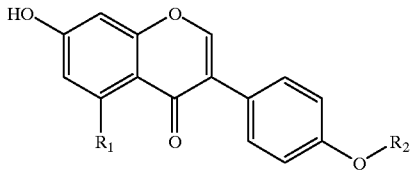

wherein
$R_1$=OH and $R_2$=H, Genistein;
$R_1$=H and $R_2$=H, Daidzein;
$R_1$=H and $R_2$=$CH_3$, Formononetin; and
$R_1$=OH and $R_2$=$CH_3$, Biochanin A.

It is known that isoflavones belong to the class of phytoestrogens or plant oestrogens. These are particularly useful thanks to their pharmacological and therapeutic properties such as, for example, their anti-cancer and oestrogen activity (WO 99/48496, WO 99/43335 and WO 93/23069).

Such properties have been mainly attributed to the aglycone form of the isoflavones, i.e. to the isoflavone moiety without the sugar moiety.

In nature, isoflavones are present in many plant materials such as, for example, *Trifolium pratense, Trifolium subterranean, Abrus precatorius*, various species of Acacia, *Apio tuberosa, Arachis hypogea, Astragalus edulis, Bauhinina esculenta, Cajanus cajan indicus, Canavalia ensiformis, Canavalia gladiata, Canavalia rosea*, varies species of Cassia, *Ceratonia siliqua, Cicer arietinum, Cordeauxia edulis*, various species of Crotalaria, *Cyramopsis psoralioides, Detariaum senegalese, Entada scandes, Erythrina edulis, Glycine max*, Ingaedulis, *Inocarpus fagifer, Lablab purpureus, Lathyrus sativus, Lathyrus ochrus, Lens culinaris, Leucaenal eucocephala*, various species of Lupinus, *Macatylma geacapra, Macrotyloma uniflorum, Medicago sativa, Mucuna pruriens, Pachyrhyzuz erosus, Parkia clappertoniana, Parkia speciosa, Pentaclethra macrophylla*, various species of Phaseolus, *Pisum sativum, Pithecolobium lobatum*, various species of Prosopis, *Psophocarpus scandens*, various species of Psoralea, *Sesbania bispinosa, Sphenostylis stenocarpa, Tamarindus indica, Trigonella foenum-graecum*, various species of Vivia, *Vicia faba, Vigna mungo*, various speices of Vigna and *Voandzeia subterranea*.

Patent application WO 93/23069 describes compositions that are rich in natural phytoestrogens or analogues thereof, such as Genistein, Daidzein, Formononetin and Biochanin A.

These phytoestrogens are obtained by:
a) drying the plant material;
b) extracting it with a mixture of water and a water-miscible organic solvent (60% ethanol, Example 1);
c) separating the extract from the undissolved plant material and removing the organic solvent; and
d) concentrating the aqueous phase.

However, in the said document, the extraction yield is never indicated and it is not specified whether the isoflavones are obtained as aglycones or in glycosylated form.

Patent application WO 99/43335 describes compositions of an extract of clover from which have been isolated compounds containing aromatic chromophoric groups such as the isoflavones Genistein, Daidzein, Formononetin and Biochanin and/or glucosides thereof. The said extract has anticancer activity against one or more HL60, K562, LNCaP or HT29 cell lines. The said composition is optionally in combination with a pharmaceutically acceptable carrier, auxiliary excipients and/or diluents.

This extract is prepared by:
a) drying the plant material;
b) extracting the thus obtained material with a mixture of water and a water-miscible organic solvent (60% ethanol, Example 1);
c) separating the extract from the undissolved plant material and removing the organic solvent;
d) extracting the aqueous phase with an organic solvent such as petroleum ether;
e) removing the organic solvent;
f) drying the aqueous phase; and
g) separating the isoflavones containing aromatic chromophoric groups by HPLC (page 6, lines 10–29).

This document too never indicates the extraction yield. In addition, even the experimental section fails to indicate whether the isoflavones are obtained as aglycones or in glycosylated form.

International patent application WO 99/48496 describes a method for the treatment, prophylaxis, improvement or prevention of conditions associated with an abnormally high activity of steroidal oestrogens, the said method comprising the administration of a composition of an extract containing clover or chick pea isoflavones, the said extract mainly comprising biochanin, or a biochanin/formononetin, daidzein and genistein ratio of between 2:1 and 5:1 approximately, optionally in combination with a pharmaceutically acceptable carrier, auxiliary excipients and/or diluents.

This extract is prepared by:
a) freezing the fresh plant material with liquid nitrogen;
b) grinding the thus obtained material;
c) extracting the thus obtained material with a mixture of water and a water-miscible organic solvent (60% ethanol, Example 1);
d) separating the extract from the undissolved plant material and removing the organic solvent;
e) extracting the aqueous phase with an organic solvent such as petroleum ether, hexane or ethyl acetate;
f) removing the organic solvent; and
g) drying the aqueous phase (page 8, lines 4–32).

However, the extraction yield is never indicated in this document. In addition, in the experimental section it is reported that the aqueous phase contains the isoflavones as aglycones (Example 1, page 12, line 26). However, this must be an entirely negligible amount since it is known that the aglycones are substantially insoluble in water.

There is therefore still a great need for a dry extract containing at least 8% (w/w) of one or more isoflavones, as aglycones, and for a process for preparing the same.

It has now been surprisingly found that this result is achieved if, before extracting the isoflavones with an organic solvent, the dry plant material undergoes a maceration in water, preferably under an inert atmosphere and in a vessel protected against light. Indeed, it has been found that the isoflavone moiety separates from the sugar moiety in said maceration step. The reason for this has still not been fully understood but, without hereby limiting the present invention, it is opined that the isoflavone-sugar link is labile enough to be hydrolysed in water and/or that the plant material contains an enzyme capable of hydrolysing the abovementioned link.

It is, therefore, a first object of the present invention to provide a process for extracting isoflavones from a plant material, wherein the said process comprises treating the plant material with an organic solvent, characterized in that the said extraction is preceded by a maceration step in water.

The said organic solvent is preferably miscible with water.

Typical examples of the said water-miscible organic solvents are alkanols having from 1 to 4 carbon atoms such as, for example, methanol, ethanol, propanol and butanol. Other typical examples of the said solvents are propylene glycol, erythritol, butanediol, acetonitrile, ethylene glycol, ethyl acetate, glycidol, dihydroxyacetoneglycerol and acetone.

Advantageously, the plant material, which undergoes maceration, is in dry form. Even more advantageously, the plant material is also ground up.

The said maceration is preferably carried out under an atmosphere of an inert gas such as nitrogen.

According to a preferred embodiment, the said maceration is carried out in a vessel protected against light.

The said maceration is advantageously carried out at a temperature of from 20° C. to 30° C.

The maceration time may vary within a wide range depending on parameters that are well known to those skilled in the art, such as, for example, the temperature and volume of water present per unit by weight of dry plant material. As a guide, this time is of from 10 minutes to 24 hours. This time is preferably of from 2 to 6 hours.

The abovementioned maceration is typically followed by the following steps:
a) extraction with at least one water-miscible organic solvent,
b) separation of the undissolved plant material,
c) treatment of the solution obtained in step b) with an aliphatic hydrocarbon having from 5 to 8 carbon atoms, and
d) removal of the solvent in order to obtain a solid residue.

The thus obtained solid residue contains at least 8% (w/w) of one or more isoflavones in the form of aglycones.

The treatment in the abovementioned step c) is mainly intended to remove the essential oils such as, for example, terpenes, and waxes.

The aliphatic hydrocarbon in the abovementioned step c) is preferably n-heptane.

After step d), the following steps may optionally also be carried out:
e) optionally, redissolution of the solid residue from step d) in a water-miscible organic solvent,
f) extraction of the solution obtained in step e) with a suitable organic solvent, and
g) removal of the solvent in order to obtain a solid residue.

Suitable solvents which may be used in the abovementioned step f) are those which have high affinity for isoflavones in the form of aglycones, such as, for example, methyl tert-butyl ether and ethyl acetate.

It is, therefore, a further object of the present invention to provide a dry extract containing, as aglycones, at least 8% (w/w) of one or more isoflavones of formula

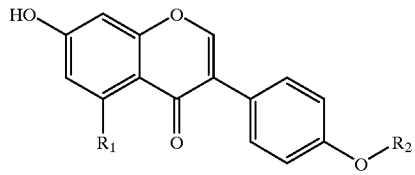

wherein
$R_1$=OH and $R_2$=H, Genistein;
$R_1$=H and $R_2$=H, Daidzein;
$R_1$=H and $R_2$=CH$_3$, Formononetin;
$R_1$=OH and $R_2$=CH$_3$, Biochanin A.

The amount of the abovementioned aglycones is preferably greater than 15% (w/w).

The examples which follow are given to illustrate the present invention without, however, limiting it in any way.

EXAMPLE 1

Preparation of a dry extract of *Trifolium pratense* (titre of isoflavones as aglycones=19.5 w/w %)

Dried *Trifolium pratense* (500 g), containing about 0.1% (w/w) of total free aglycone isoflavones assayed by HPLC as the sum of Biochanin, Formononetin, Daidzein and Genistein, was ground up in order to obtain a fine powder.

The powder then underwent maceration by impregnating it homogeneously with tap water (2000 ml) and was kept at 25° C. for 3.5–4 hours under a nitrogen atmosphere.

95% ethanol (3000 ml) was then added to the aqueous mixture. The first extraction of the organic phase was carried out by boiling the aqueous-alcoholic solution for 3 hours. The plant material then underwent two successive extractions with 80% ethanol (2×2000 ml).

The combined organic extracts were treated with n-heptane (3×1000 ml). The heptane solution was discarded, while the aqueous-alcoholic solution was concentrated by evaporation (at a residual pressure of 26,600 pascals) to a final volume of 500 ml, cooled to 5° C. for 1 hour and filtered. The obtained solid was washed with cold water (50 ml) and oven-dried at a residual pressure of about 660 pascals.

22.0 g of dry extract were thus obtained (yield=4.4% by weight relative to the weight of the starting dry *Trifolium pratense*) having a titre, by HPLC, of isoflavones as aglycones of 19.5% (w/w) [about 9% (w/w) of Biochanin, about 8% (w/w) of Formononetin, about 1% (w/w) of Daidzein and about 1.5% (w/w) of Genistein].

The yield of isoflavones as aglycones is thus about 0.86% (19.5%×4.4%) relative to the weight of the starting dry plant material.

EXAMPLE 2

Preparation of a dry extract of *Trifolium pratense* (titre of isoflavones as aglycones=21.6 w/w %)

The process was performed in a manner similar to that described in Example 1 above, except that the starting dried *Trifolium pratense* (500 g) contained about 0.05% (w/w) of total free aglycone isoflavones, assayed by HPLC as the sum of Biochanin, Formononetin, Daidzein and Genistein.

17.5 g of dry extract were thus obtained (yield=3.5% by weight relative to the weight of the starting dry *Trifolium*

*pratense*) with a titre, by HPLC, of isoflavones as aglycones of 21.6% (w/w) [about 10% (w/w) of Biochanin, about 9% (w/w) of Formononetin, about 1% (w/w) of Daidzein and about 1.5% (w/w) of Genistein].

The yield of isoflavones as aglycones is thus about 0.76% (21.6%×3.5%) relative to the weight of the starting dry plant material.

EXAMPLE 3

Preparation of a dry extract of *Trifolium pratense* (titre of isoflavones as aglycones=38 w/w %)

The dry extract of *Trifolium pratense* (10 g) obtained as described in Example 1 (titre of isoflavones as aglycones of 19.5 w/w %) was treated with a mixture of 95% ethanol (200 ml), tap water (600 ml) and sodium chloride (0.5 g). The thus obtained mixture underwent extraction with methyl tert-butyl ether (3×400 ml). The combined ether extracts were washed with 20% ethanol (200 ml). The ether solution was separated out and concentrated under vacuum to give a dry residue. The dry residue was oven-dried under a residual vacuum of about 660 pascals.

5.0 g of dry extract were thus obtained (yield=50% by weight relative to the weight of the starting dry extract of *Trifolium pratense* and yield=2.2% by weight relative to the starting 500 g of *Trifolium pratense* from Example 1) having a titre, by HPLC, of isoflavones as aglycones of 38% (w/w) [about 18% (w/w) of Biochanin, about 16% (w/w) of Formononetin, about 1.5% (w/w) of Daidzein and about 2.5% (w/w) of Genistein].

EXAMPLE 4

Preparation of a dry extract of *Trifolium pratense* (titre of isoflavones as aalycones=32 w/w %)

The process was performed in a manner similar to that described in Example 3 above, except that ethyl acetate (3×400 ml) was used instead of methyl tert-butyl ether.

6.0 g of dry extract were thus obtained (yield=60% by weight relative to the weight of the starting dry extract of *Trifolium pratense* and yield=2.64% by weight relative to the starting 500 g of *Trifolium pratense* from Example 1) having a titre, by HPLC, of isoflavones as aglycones of 32% (w/w) [about 15% (w/w) of Biochanin, about 13% (w/w) of Formononetin, about 2% (w/w) of Daidzein and about 2% (w/w) of Genistein].

COMPARATIVE EXAMPLE 1

Preparation of a dry extract of *Trifolium pratense*

Dried *Trifolium pratense* (50 g) from the same batch as that used in Example 1 was used as starting plant material. This material was ground up until a fine powder was obtained and was then extracted with boiling (95° C.) 60% ethanol (3×500 ml) for 2 hours.

The combined and cooled organic extracts were treated with n-heptane (3×100 ml). The heptane solution was discarded, while the alcoholic solution was concentrated by evaporation (at a pressure of about 26,600 pascals) to a final volume of 1/10 of its initial volume, and cooled at 5° C. for 1 hour. In contrast with Example 1, no precipitate was obtained.

The aqueous-alcoholic solution was then concentrated to give a dry residue.

14.02 g of dry residue were thus obtained (yield=28% by weight relative to the weight of the starting dry *Trifolium pratense*) having a titre, by HPLC, of isoflavones as aglycones of 0.4% (w/w) [about 0.2% (w/w) of Biochanin, about 0.18% (w/w) of Formononetin, about 0.01% (w/w) of Daidzein and about 0.01% (w/w) of Genistein].

The yield of isoflavones as aglycones is thus about 0.11% (28%×0.4%) relative to the weight of the starting dry plant material.

COMPARATIVE EXAMPLE 2

Preparation of a dry extract of *Trifolium pratense*

The process was performed in a manner similar to that described in Comparative Example 1, to give an aqueous-alcoholic solution treated with n-heptane.

This solution (1500 ml) was then concentrated under a reduced pressure of about 26,600 pascals, to a residual volume of about 300 ml. The amount of ethanol was adjusted to 20% and this solution was then extracted with methyl tert-butyl ether (3×150 ml).

The ether extracts were combined, washed with water (150 ml) and concentrated under a reduced pressure of about 26,600 pascals until a dry residue was obtained.

1.85 g of dry extract were thus obtained (yield=3.7% by weight relative to the weight of the starting dry *Trifolium pratense*) having a titre, by HPLC, of isoflavones as aglycones of 3.1 w/w% [about 1.6% (w/w) of Biochanin, about 1.4% (w/w) of Formononetin, about 0.05% (w/w) of Daidzein and about 0.05% (w/w) of Genistein].

The yield of isoflavones as aglycones is thus about 0.1147% (3.7%×3.1%) relative to the weight of the starting dry plant material.

What is claimed is:

1. In a process for extracting isoflavones from a plant material, wherein the said process comprises treating the plant material with an organic solvent to produce an extract, characterized in that the said organic solvent extraction is preceded by a step of maceration in water in the absence of an organic solvent.

2. A process according to claim 1, characterized in that the said plant material is chosen from the group consisting of *Trifolium pratense, Trifolium subterranean, Abrus precatorius*, various species of Acacia, *Apio tuberosa, Arachis hypogea, Astragalus edulis, Bauhinina esculenta, Cajanus cajan indicus, Canavalia ensiformis, Canavalia gladiata, Canavalia rosea*, varies species of Cassia, *Ceratonia siliqua, Cicer arietinum, Cordeauxia edulis*, various species of Crotalaria, *Cyramopsis psoralioides, Detariaum senegalese, Entada scandes, Erythrina edulis, Glycine max*, Ingaedulis, *Inocarpus fagifer, Lablab purpureus, Lathyrus sativus, Lathyrus ochrus, Lens culinaris, Leucaenal eucocephala*, various species of Lupinus, *Macatylma geacapra, Macrotyloma uniflorum, Medicago sativa, Mucuna pruriens, Pachyrhyzuz erosus, Parkia clappertoniana, Parkia speciosa, Pentaclethra macrophylla*, various species of Phaseolus, *Pisum sativum, Pithecolobium lobatum*, various species of Prosopis, *Psophocarpus scandens*, various species of Psoralea, *Sesbania bispinosa, Sphenostylis stenocarpa, Tamarindus indica, Trigonella foenum-graecum*, various species of Vivia, *Vicia faba, Vigna mungo*, various speices of Vigna and *Voandzeia subterranea*.

3. A process according to claim 2, characterized in that the said plant material is *Trifolium pratense*.

4. A process according to according to claim 1, characterized in that the said maceration is carried out under an atmosphere of an inert gas.

5. A process according to claim 4, characterized in that the said inert gas is nitrogen.

6. A process according to claim 1, characterized in that the said maceration is carried out in a vessel protected against light.

7. A process according to claim 1, characterized in that the said maceration is carried out at a temperature of from 20° C. to 30° C.

8. A process according to claim 1, characterized in that the said maceration is carried out for a period of time from 10 minutes to 24 hours.

9. A process according to claim 8, characterized in that the said maceration is carried out for a period of time of from 2 to 6 hours.

10. A process according to claim 1, characterized in that the said maceration is followed by the following steps:
    (a) subjecting the macerated plant material to extraction with at least one water-miscible organic solvent to produce a solution of the extract,
    (b) separation of the undissolved plant material from the solution,
    (c) treatment of the solution obtained in step (b) with an aliphatic hydrocarbon having from 5 to 8 carbon atoms to obtain a treated solution, and
    (d) removal of the solvent from the treated solution in order to obtain a solid residue.

11. A process according to claim 10, characterized in that the said aliphatic hydrocarbon in step c) is n-heptane.

12. A dry extract of plant material containing, as aglycones, at least 8% (w/w) of one or more isoflavones of formula

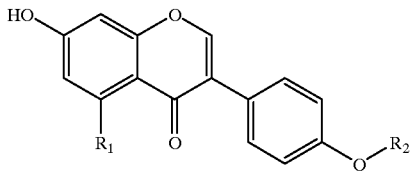

wherein
$R_1$=H and $R_2$=$CH_3$, Formononetin;
$R_1$=OH and $R_2$=$CH_3$, Biochanin A.

13. A dry extract according to claim 12, characterized in that the amount of the said aglycones is greater than 15% (w/w).

14. A process according to claim 5, characterized in that the said maceration is carried out in a vessel protected against light.

15. A process according to claim 14, characterized in that the said maceration is carried out at a temperature of from 20° C. to 30° C.

16. A process according to claim 15, characterized in that the said maceration is carried out for a period of time of from 10 minutes to 24 hours.

17. A process according to claim 16, characterized in that the said maceration is carried out for a period of time of from 2 to 6 hours.

18. A process according to claim 1 characterized in that the said maceration produces an aqueous mixture of the plant material and is followed by the following steps:
    (a) addition of at least one water-miscible organic solvent to the aqueous mixture and subjecting the plant material to extraction with the water-water-miscible organic solvent mixture to produce a solution of the extract,
    (b) separation of the undissolved plant material from the solution,
    (c) treatment of the solution obtained in step (b) with an aliphatic hydrocarbon having 5 to 8 carbon atoms to obtain a treated solution, and
    (d) removal of the solvent from the treated solution to obtain a solid residue containing extracted isoflavones.

19. Process according to claim 18 wherein the following further steps are carried out,
    (e) redissolving the solid residue from step (d) in a mixture of water and a water-miscible organic solvent,
    (f) subjecting the solution obtained in step (e) to extraction with a solvent having a high affinity for isoflavones in the form of aglycones to obtain a solution (f), and
    (g) removal of the solvent from the solution (f) to obtain a solid residue.

20. Process according to claim 18 wherein the water-miscible organic solvent is ethanol.

21. A process according to claim 17 characterized in that the said maceration produces an aqueous mixtures of the plant material and is followed by the followng steps:
    (a) addition of at least one water-miscible organic solvent to the aqueous mixture and subjecting the plant material to extraction with the water-water-miscible organic solvent mixture to produce a solution of the extract,
    (b) separation of the undissolved plant material from the solution,
    (c) treatment of the solvent obtained in step (b) with an aliphatic hydrocarbon having 5 to 8 carbon atoms to obtain a treated solution, and
    (d) removal of the solvent from the water solution to obtain a solid residue containing extracted isoflavones.

22. Process according to claim 21 wherein the following addition further steps are carried out,
    (e) redissolving the solid residue from step (d) in a mixture of water and a water-miscible organic solvent,
    (f) extraction of the solution obtained in step (e) with a solvent having a high affinity for isoflavones in the form of aglycones to obtain a solution (f) and
    (g) removal of the solvent from the solution (f) to obtain a solid residue.

23. Process according to claim 21 wherein the water-miscible organic solvent is ethanol.

24. In a process for extracting isoflavones from a plant material of the genus Trifolium, wherein the said process comprises treating the plant material with an organic solvent to produce an extract, characterized in that the said organic solvent extraction is preceded by a step of maceration in water in the absence of an organic solvent.

25. A process according to claim 4, characterized in that said maceration is carried out under an atmosphere of an inert gas.

26. A process according to claim 25, characterized in that the said inert gas is nitrogen.

27. A process according to claim 24, characterized in that said maceration is carried out in a vessel protected against light.

28. A process according to claim 24, characterized in that the said maceration is carried out at a temperature of from 20° C. to 30° C.

29. A process according to claim 24, characterized in that the said maceration is carried out for a period of time of from 10 minutes to 24 hours.

30. A process according to claim 29, characterized in that the said maceration is carried out for a period of time of from 2 to 6 hours.

31. A process according to claim 24, characterized in that the said maceration is followed by the following steps:
    a) extraction with at least one water-miscible organic solvent, b) separation of the undissolved plant material, c) treatment of the solution obtained in step b) with an aliphatic hydrocarbon having from 5 to 8 carbon atoms, and d) removal of the solvent in order to obtain a solid residue.

32. A process according to claim 31, characterized in that the said aliphatic hydrocarbon in step c) is n-heptane.

33. A process according to claim 26, characterized in that the said maceration is carried out in a vessel protected against light.

34. A process according to claim 33, characterized in that the said maceration is carried out at a temperature of from 20° C. to 30° C.

35. A process according to claim 34, characterized in that the said maceration is carried out for a period of time of from 10 minutes to 24 hours.

36. A process according to claim 35, characterized in that the said maceration is carried out for a period of time of from 2 to 6 hours.

37. A process according to claim 24 characterized in that the said maceration produces an aqueous mixture of the plant material and is followed by the following steps:

(a) addition of at least one water-miscible organic solvent to the aqueous mixture and subjecting the plant material to extraction with the water-water-miscible organic solvent mixture to produce a solution of the extract, (b) separation of the undissolved plant material from the solution, (c) treatment of the solution obtained in step (b) with an aliphatic hydrocarbon having 5 to 8 carbon atoms to obtain a treated solution, and (d) removal of the solvent from the treated solution to obtain a solid residue containing extracted isoflavones.

38. Process according to claim 37 wherein the following further steps are carried out, (e) redissolving the solid residue from step (d) in a mixture of water and a water-miscible organic solvent, (f) subjecting the solution obtained in step (e) to extraction with a solvent having a high affinity for isoflavones in the form of aglycones to obtain a solution (f), and (g) removal of the solvent from the solution (f) to obtain a solid residue.

39. Process according to claim 37 wherein the water-miscible organic solvent is ethanol.

40. A process according to claim 36 characterized in that the said maceration produces an aqueous mixture of the plant material and is followed by the following steps:

(a) addition of at least one water-miscible organic solvent to the aqueous mixture and subjecting the plant material to extraction with the water-water-miscible organic solvent mixture to produce a solution of the extract, (b) separation of the undissolved plant material from the solution, (c) treatment of the solvent obtained in step (b) with an aliphatic hydrocarbon having 5 to 8 carbon atoms to obtain a treated solution, and (d) removal of the solvent from the water solution to obtain a solid residue containing extracted isoflavones.

41. Process according to claim 40, wherein the following additional further steps are carried out, (e) redissolving the solid residue from step (d) in a mixture of water and a water-miscible organic solvent, (f) extraction of the solution obtained in step (e) with a solvent having a high affinity for isoflavones in the form of aglycones to obtain a solution (f) and (g) removal of the solvent from the solution (f) to obtain a solid residue.

42. Process according to claim 40, wherein the water-miscible organic solvent is ethanol.

* * * * *